United States Patent
Prasek et al.

(10) Patent No.: US 8,465,984 B2
(45) Date of Patent: Jun. 18, 2013

(54) METHOD OF DETECTING AN EMULSION IN BRINE

(75) Inventors: Bethicia B. Prasek, The Woodlands, TX (US); Marc A. Churan, Houston, TX (US)

(73) Assignee: M-I L.L.C, Houston, TX (US)

( * ) Notice: Subject to any disclaimer, the term of this patent is extended or adjusted under 35 U.S.C. 154(b) by 209 days.

(21) Appl. No.: 13/131,979

(22) PCT Filed: Jan. 25, 2010

(86) PCT No.: PCT/US2010/021970
§ 371 (c)(1),
(2), (4) Date: May 31, 2011

(87) PCT Pub. No.: WO2010/085740
PCT Pub. Date: Jul. 29, 2010

(65) Prior Publication Data
US 2011/0235021 A1    Sep. 29, 2011

Related U.S. Application Data

(60) Provisional application No. 61/147,144, filed on Jan. 26, 2009.

(51) Int. Cl.
*G01N 21/00* (2006.01)

(52) U.S. Cl.
USPC ............... 436/164; 702/12; 702/25; 702/30; 702/50; 166/264

(58) Field of Classification Search
None
See application file for complete search history.

(56) References Cited

U.S. PATENT DOCUMENTS

| | | | |
|---|---|---|---|
| 6,884,760 B1 | 4/2005 | Brand et al. | |
| 2004/0098202 A1 | 5/2004 | McNeil et al. | |
| 2008/0133193 A1 | 6/2008 | Gdanski et al. | |
| 2008/0135302 A1 | 6/2008 | Zhang et al. | |

OTHER PUBLICATIONS

International Search Report and Written Opinion, dated Sep. 7, 2010, for PCT/US2010/021970.

*Primary Examiner* — Robert Xu
(74) *Attorney, Agent, or Firm* — Sara M. Hinkley

(57) ABSTRACT

The instant disclosure is directed to a method of detecting an emulsion in a turbid brine, the method comprising the steps of disposing an aliquot of the turbid brine into a sample container to produce a test sample; adding one or more drops of a dye solution comprising an oil-soluble dye dissolved in a nonaqueous base fluid to said test sample; and determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine.

34 Claims, 1 Drawing Sheet

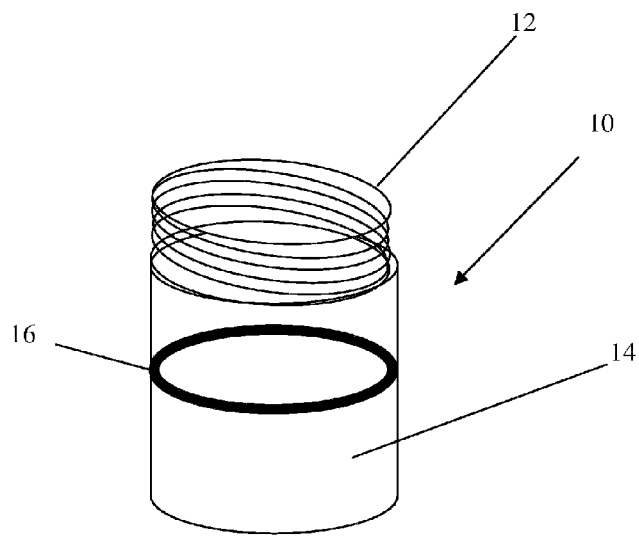
FIG. 1
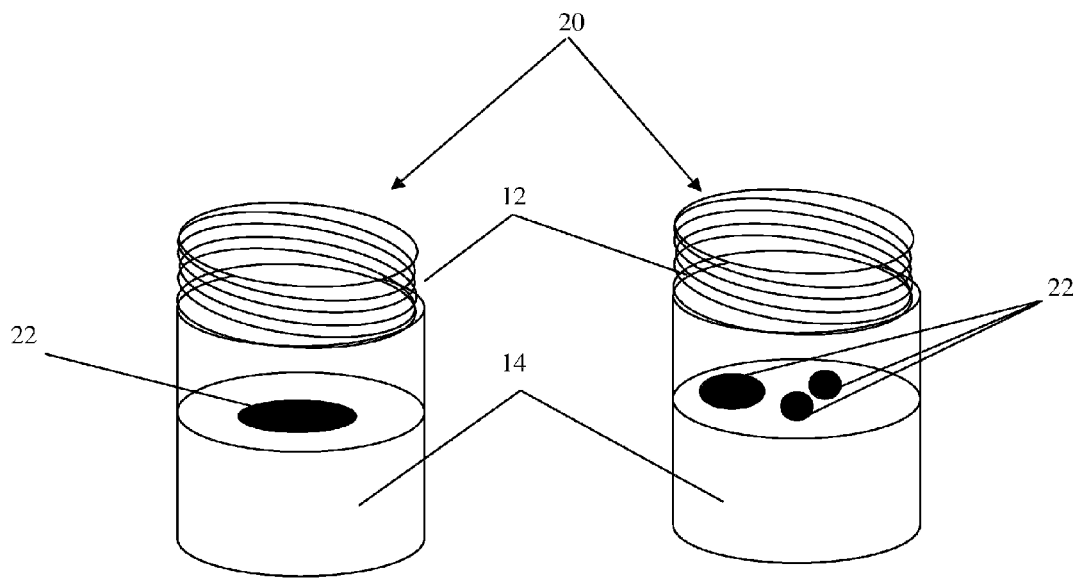
FIG. 2a  FIG. 2b

METHOD OF DETECTING AN EMULSION IN BRINE

BACKGROUND OF INVENTION

1. Field of the Invention

This invention relates to a method of detecting the presence of an emulsion in a brine. In particular, a method of detecting the presence of an emulsion in a turbid brine. This invention further relates to a method of differentiating between suspended particulate matter and the presence of an emulsion being the cause of turbidity in a completion brine.

2. Background Art

During the drilling of a wellbore, various fluids are typically used in the well for a variety of functions. The fluids may be circulated through a drill pipe and drill bit into the wellbore, and then may subsequently flow upward through wellbore to the surface. During this circulation, the drilling fluid may act to remove drill cuttings from the bottom of the hole to the surface, to suspend cuttings and weighting material when circulation is interrupted, to control subsurface pressures, to maintain the integrity of the wellbore until the well section is cased and cemented, to isolate the fluids from the formation by providing sufficient hydrostatic pressure to prevent the ingress of formation fluids into the wellbore, to cool and lubricate the drill string and bit, and/or to maximize penetration rate.

Drilling of an oil will proceeds in numerous steps. Once drilling operations of an oil well have been completed, the well is prepared for the completion operations, whereby the mud used for drilling is often displaced by a completion fluid. There are numerous methods of completing a well, amongst which are open hole completions, pre-drilled, liner, gravel packed screened systems, and the like. Clear, solids-free brines are used as completion/workover fluids for the purpose of controlling downhole formation pressures while reducing the risk of permanent formation damage resulting from solids invasion. These clear brine completion fluids are formulated and maintained to specifications which include density and clarity.

Determinations of well completion may be made via analysis of the completion fluid. Typically, a limit on the turbidity of the completion fluid is set, such that when the turbidity of the completion fluid falls below a certain level, the materials which were being removed by the completion fluid are considered to have been removed. Accordingly, once the turbidity of the completion fluid falls below a prescribed level, this part of the drilling process is complete.

Use of lubricants, petroleum coming from the well itself, and/or other additives used during one or more steps of the well drilling process may result in emulsions being formed within the completion fluid. Emulsions in completion fluids may result in turbid solutions, which resemble completion fluids emanating from a well which is not yet complete. The formation of a stable emulsion in a completion fluid thus frustrates the ability of those completing the well to determine when all the particulate matter has been removed from the well and thus, determining when this phase of the process has run to completion.

Accordingly, a need exists for a method of determining and/or differentiating between an emulsion and particulate matter in a brine, preferably in a completion fluid.

SUMMARY OF INVENTION

In a first aspect of the present invention, a method of detecting an emulsion in a turbid brine comprises the steps of:

disposing an aliquot of the turbid brine into a sample container to produce a test sample;

adding one or more drops of a dye solution comprising an oil-soluble dye dissolved in a base oil to said test sample; and determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine.

In another aspect of the present invention, a method of detecting an emulsion in a turbid brine comprises the steps of:

passing an aliquot of the turbid brine through a 0.1 to 10 micron filter to produce a filtered aliquot;

disposing at least a portion of the filtered aliquot into a sample container to produce a test sample;

adding one or more drops of a dye solution comprising an oil-soluble dye dissolved in a base oil to said test sample; and determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine.

In still another aspect of the present invention, a method of determining the turbidity of a turbid brine comprises the steps of:

disposing an aliquot of the turbid brine into a sample container to produce a test sample;

adding one or more drops of a dye solution comprising an oil-soluble dye dissolved in a base oil to said test sample; and determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine;

disposing another aliquot of the turbid brine into a sample container along with an aliquot of an emulsion breaking solvent to produce a centrifuge sample;

mixing the centrifuge sample by agitation, shaking, or the like;

centrifuging the centrifuge sample for a period of time to sufficiently remove solids which may be present in the turbid brine;

determining the presence of solids which may be been separated from the turbid brine after centrifuging; and removing a portion of the brine from the centrifuge sample and determining the turbidity of the brine.

These and other features, aspects and advantages of the present invention will become better understood with reference to the following drawings, description and claims

BRIEF DESCRIPTION OF THE DRAWINGS

FIG. 1 depict a positive test sample of the instant invention; and

FIGS. 2a and 2b depict negative test samples of the instant invention.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

In the following description, numerous specific details are set forth to provide a thorough understanding of the present invention. However, it will be obvious to those skilled in the art that the present invention may be practiced without such specific details. In other instances, well-known devices have been shown in block diagram form in order not to obscure the present invention in unnecessary detail. For the most part, details unnecessary to obtain a complete understanding of the present invention have been omitted in as much as such details are within the skills of persons of ordinary skill in the relevant art.

Broadly, the present invention generally provides for a method of detecting an emulsion in a turbid brine. In an embodiment, the method comprises the step of contacting a turbid brine with one or more drops of a dye solution comprising an oil-soluble dye dissolved in a nonaqueous base fluid. The method may further include the step of determining the configuration of the dye solution after a period of time on a surface of the test sample, wherein a configuration of the dye solution forming a ring around the perimeter of the container in which the turbid brine is being kept. This ring may present itself at the interface of the container wall and the turbid brine, and indicates an emulsion is present in the turbid brine. When the dye solution does not form a ring, but instead forms a single "dot" or a plurality of dots on the surface of the turbid brine, an emulsion is not present in the turbid brine.

In an embodiment, the instant method may comprise the steps of disposing an aliquot of the turbid brine into a sample container to produce a test sample. Next, one or more drops of a dye solution comprising an oil-soluble dye dissolved in a nonaqueous base fluid are added (i.e., contacted with) the test sample. Next, the configuration of the dye solution is determined after a period of time on a surface of the test sample. A configuration of the dye solution forming a ring around the perimeter of the container at the interface of the container wall and the turbid brine indicates an emulsion is present in the turbid brine. A configuration of the dye solution forming a single dot or a plurality of dots on the surface of the turbid brine indicates an emulsion is not present in the turbid brine.

Preferably, the sample container is a clean glass testing vial. Suitable examples include glass vials capable of holding about 20 ml of liquid. Examples include scintillation vials, test tubes, centrifuge tubes, and the like. The sides of the container are preferably transparent to allow for detection of the ring of dye at the container wall—liquid interface, or the "dot" of dye floating on the surface of the liquid.

Suitable sample volumes for the instant method are typically on the order of about 10 mls, however, the instant method need not be limited as such, so long as a proper determination may be made. Accordingly, in an embodiment, the test sample comprises a 20 ml scintillation vial filled about halfway with the turbid brine.

In an embodiment, the turbid brine is preferably a completion fluid. In an embodiment, completion fluids may comprise a halide salt, a formate salt, or any combination thereof. In an embodiment, the turbid brine comprises an aqueous solution comprising of sodium chloride, sodium bromide, sodium formate, potassium chloride, potassium bromide, potassium formate, cesium chloride, cesium bromide, cesium formate, calcium chloride, calcium bromide, zinc chloride, zinc bromide, or any combination thereof. The turbid brine may be characterized as having a turbidity of greater than 20 Nephelometric Turbidity Units (NTU) as determined by methods well known to those skilled in the art.

In an embodiment, the turbid brine is taken from an oil well in which a lubricant and/or a material designed to reduce the coefficient of friction on equipment was used in combination with a completion fluid during completion of the well. Examples of such lubricants include Safe Lube, commercially available from MI SWACO, Houston, Tex.

Suitable dyes for use herein include so-called oil soluble dyes, which are characterized as having limited, if any water solubility, yet are soluble in non-polar organic solvents. Preferably, the oil-soluble dyes are soluble in the drilling base oil used in drilling the well from which a sample of brine is being evaluated. Suitable oil-soluble dyes include lysochromes, fat-soluble dyes, solvent dyes, and the like. Accordingly, preferred dye solutions may comprise one or more oil soluble dyes, including one or more lysochromes, fat-soluble dyes, solvent dyes, and the like. Preferred examples of oil-soluble dyes include one or more of:

Oil Red O, also known as Solvent Red 27, and Sudan Red 5B, having the empirical formula $C_{26}H_{24}N_4O$, which has the following structure:

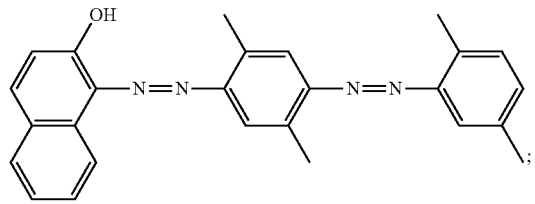 [SMILES: Cc1ccc(C)c(N=Nc2cc(C)c(N=Nc3c(O)ccc4ccccc34)cc2C)c1]

the various Sudan dyes, including Sudan IV, having the empirical formula $C_{24}H_{20}N_4O$, which has the following structure:

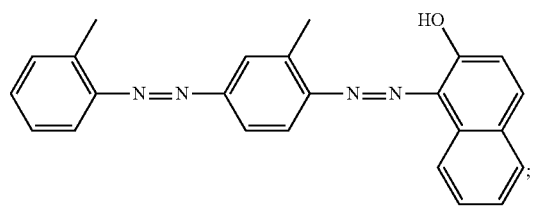 [SMILES: Cc1ccccc1N=Nc1ccc(N=Nc2c(O)ccc3ccccc23)c(C)c1]

and Oil Blue N, having the empirical formula $C_{24}H_{30}N_2O_2$, which has the following structure:

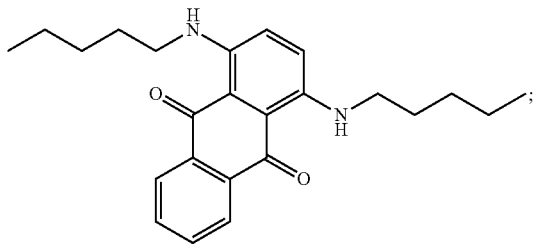 [SMILES: CCCCCNc1ccc(NCCCCC)c2c1C(=O)c1ccccc1C2=O]

and the like.

Other examples of suitable oil-soluble dyes for use in dye solutions herein include lysochrome dyes. Suitable dye solutions may comprise one or more of the following lysochrome dyes:

Giemsa (May-Greenwald's) stain or Sudan Black; Sudan I; Nigrosine; Sudan II; Neozapan Red GE; Oil Blue A; Oil Blue N, Methyl Violet 1 B; Sudan Red BB; Sudan Orange G; para-phenylazophenol; Rose Bengal; 4',5'-dibromofluoroscein; Sudan Red 7B; Sudan Black B; Sudan Yellow 146; Neozapan Blue; Oracet Yellow GN; Sudan Yellow 150; Sudan Red 7B; Oil Yellow; Ceres Red 3R; Oil Pink 312; Pylakrome Pink LX 1900; Ceres Blue R; Neozapan 807; Sudan Deep Black; Ceres Black BN; combinations thereof, and the like.

So called solvent dyes are also suitable for use herein. Suitable dye solutions may comprise one or more of the following solvent dyes:

Solvent Oil yellow G; CAS#60-11-7; Solvent Fluorescent Yellow 8GF; CAS#85-84-7; Solvent Oil Yellow R; CAS#842-07-9; Solvent Oil Yellow 3G; CAS#4314-14-1; Solvent Spirit Light Fast Yellow GR; CAS#10343-55-2; Solvent Yellow BL; CAS#5601-29-6; Solvent Yellow 4G; CAS#8003-22-3; Solvent Oil Golden Yellow 2G; CAS#2481-94-9; Solvent Transparent Yellow 2 GH; CAS#61813-98-7; Solvent Yellow KR; CAS#12227-67-7; Solvent Transparent Yellow 3G; CAS#4702-90-3; Solvent Fluorescent Yellow 3G; CAS#12671-74-8; Solvent Yellow 3G; CAS#75216-45-4; Solvent Fluorescent Yellow 9GF; CAS#27425-55-4; Solvent Fluorescent Yellow 10GN; CAS#94945-27-4; Solvent Transparent Yellow GS; CAS#13676-91-01; Solvent Transparent Yellow 3GL; CAS#10319-14-9; Solvent Oil Orange RC; CAS#2646-17-5; Solvent Oil Orange 45; CAS#13011-62-6; Solvent Oil Orange KRV; CAS#12237-30-8; Solvent Oil Orange 3G; CAS#61969-47-9; Solvent Oil Orange R; CAS#52256-37-8; Solvent Transparent Orange 2G; CAS#16294-75-0; Solvent Oil Orange G; CAS#81-64-1; Solvent Orange R; CAS#185766-20-5; Solvent Oil Red G; CAS#1229-55-6; Solvent Fat Brown B; CAS#6535-42-8; Solvent Oil Red GB; CAS#33270-70-1; Solvent Transparent Scarlet H; CAS#85-86-9; Solvent Oil Red B; CAS#85-83-6; Solvent Transparent Red S; CAS#3176-79-2; Solvent Oil Red TXN; CAS#4477-79-6; Solvent Rhodamine B Base; CAS#509-34-2; Solvent Red 5B; CAS#81-39-0; Solvent Transparent Red GS; CAS#82-38-2; Solvent Red 2BRN; CAS#12227-55-3; Solvent Red 2BL; CAS#61725-85-7; Solvent Transparent Red EG; CAS#71902-17-5; Solvent Transparent Red FB; CAS#70956-30-8; Solvent Red KLB; CAS#71832-19-4; Solvent Transparent Red E-2G; CAS#89106-94-5; Solvent Fluorescent Red BK; CAS#52372-36-8; Solvent Fluorescent Red GK; CAS#52372-39-1; Solvent Transparent Red CHA; CAS#15958-69-6; Solvent Fluorescent Red 5B; CAS#22-75-8; Solvent Oil Violet 5BN; CAS#52080-58-7; Solvent Methyl Violet 10B Base; CAS#467-63-0; Solvent Oil Violet B; CAS#81-48-1; Solvent Violet RS; CAS#67577-84-8; Solvent Violet RR; CAS#70956-27-3; Solvent Violet 3R; CAS#61951-89-1; Solvent Transparent Violet RL; CAS#6408-72-6; Solvent Blue B Base; CAS#6786-83-0; Solvent Blue BO Base; CAS#1325-86-6; Solvent Blue B; CAS#17354-14-2; Solvent Blue AP; CAS#14233-37-5; Solvent Blue GL; CAS#12237-24-0; Solvent Blue GP; CAS#2475-44-7; Solvent Blue 2R; CAS#61969-44-6; Solvent Transparent Blue AG; CAS#6737-68-4; Solvent Blue 2B; CAS#116-75-6; Solvent Green 5B; CAS#128-80-3; Solvent Green S-G; CAS#71839-01-5; Solvent Brown 2RL; CAS#61116-28-7; Solvent Transparent Black 4B; CAS#4197-25-5; Solvent Oil Black BR; CAS#11099-03-9; Solvent Oil Black NB; CAS#8005-02-5; Solvent Black H; CAS#12237-22-8; Solvent Black N; CAS#61901-87-9; Solvent Black BC; CAS#32517-36-5; combinations thereof, and the like.

Other dyes may be suitable for use herein, so long as the dyes do not have an appreciable water solubility, and preferably are soluble in the nonaqueous base fluid used in drilling the well. Suitable nonaqueous base fluids may comprise mineral oils, diesel fuel, low-aromatic mineral oil, non-aromatic mineral oil, isomerized $C_{16}$ to $C_{18}$ alpha-olefins, or combinations thereof. The dye solution preferably comprises about 0.01 to about 1 wt % of the oil soluble dye dissolved in the solvent to form a clear solution.

Refer now to the drawings wherein depicted elements are not necessarily shown to scale and wherein like or similar elements are designated by the same reference numeral through the several views. FIG. 1 depicts a positive test sample 10, having a positive configuration for the presence of an emulsion in a turbid brine. An aliquot of a turbid brine 14 is disposed within a clean sample container 12. The dye solution is configured as a ring 16 at the interface of the container wall and turbid brine 14, indicating the presence of an emulsion in turbid brine 14.

FIGS. 2a and 2b depict negative test samples 20, having a negative configuration for the presence of an emulsion in a turbid brine. FIG. 2a shows a "dot" 22 of the dye solution floating on the surface of turbid brine 14. FIG. 2b shows a plurality of dots 22 of the dye solution floating on the surface of turbid brine 14.

The instant method may further include additional steps to determine the presence, or not, of an emulsion in a turbid brine. In an embodiment a method of detecting an emulsion in a turbid brine may comprise the steps of passing an aliquot of the turbid brine through a 0.1 to 10 micron filter to produce a filtered aliquot, followed by disposing at least a portion of the filtered aliquot into a clean sample container to produce a test sample, and then adding one or more drops of a dye solution comprising an oil-soluble dye dissolved in a base oil to the test sample and determining the configuration of the dye solution after a period of time on a surface of the test sample as described herein.

The passing of an aliquot of the turbid brine through a 0.1 to 10 micron filter may be accomplished using a syringe mounted filter, wherein the turbid brine is drawn into the syringe, the syringe fitted with the filter, and then the turbid brine pushed through the filter. In an embodiment, the filter may have a porosity of about 0.1 to about 10 microns. Within this range, a filter porosity of about 0.45 microns or less is preferred, with less than or equal to about 1 micron being more preferred, and less than or equal to about 1.6 microns being still more preferred.

In another embodiment, a method of determining the turbidity of a turbid brine may comprise the steps of disposing an aliquot of the turbid brine into a sample container to produce a test sample; adding one or more drops of a dye solution comprising an oil-soluble dye dissolved in a base oil to said test sample; and determining the configuration of the dye solution after a period of time on a surface of the test sample as described herein to determine if an emulsion is present in the brine. These steps may then be followed by the step of disposing another aliquot of the turbid brine into a sample container along with an aliquot of an emulsion breaking solvent. Suitable examples of emulsion breaking solvents include $C_6$-$C_{12}$ acyclic and/or aliphatic alkanes (e.g., hexanes, cyclohexane, heptanes, octanes, nonanes, decanes, dodecanes, and the like), ethylene glycol ethers (e.g., ethylene glycol mono-butyl ether, ethylene glycol mono-methyl ether, and the like to produce a centrifuge sample. The centrifuge sample is then mixed by agitation, shaking, or the like to produce contact between the emulsion breaking solvent and the turbid brine. Next steps include centrifuging the centrifuge sample for a period of time sufficient to remove solids which may be present in the turbid brine; determining the presence of solids which may be been separated from the turbid brine after centrifuging; and removing a portion of the brine from the centrifuge sample and determining the turbidity of the brine (e.g., the bottom phase of the centrifuge sample when the emulsion breaking solvent has a density which is less than that of the brine.) The turbidity of the brine (e.g., the bottom phase) may be determined utilizing a turbidity meter, e.g., a Hach 2100 P Turbidity Unit or equivalent, by methods and practices known to one of skill in the art, preferably according to API 13J, section 8.

EXAMPLES

The following samples and comparative samples were prepared by first producing a synthetic turbid brine according to the components listed in Table 1. The appropriate components were added to synthetic turbid brine (i.e., synthetic sea water) to produce the samples. The turbidity of each of the samples was determined using a Hach 2100 P Turbidity unit according to API 13J Section 8. Next, 10 mls of the turbid brine were transferred into a 20 ml scintillation vial. Two drops of a dye solution comprising 0.1 wt % of Oil Red O dissolved in isomerized $C_{16}$ to $C_{18}$ alpha-olefins. The configuration of the dye was then determined after a waiting time of 3 minutes. If the configuration of the dye was unclear, a second determination was made after an additional wait time of 10 minutes.

Some of the samples were further tested via the emulsion breaking procedure, wherein 7 mls of the turbid brine were added to a 15 ml centrifuge tube. 3 mls of the emulsion breaking solvent (i.e., ethylene glycol mono-butyl ether) were then added to the centrifuge tube and the entire sample shaken for about 1 min. The centrifuge tube was then centrifuged for 3 minutes and the sample allowed to stand at room temperature (i.e., 25° C.) for 10 minutes to separate. The emulsion breaking procedure was conducted using quadruple samples to provide a sufficient amount of the brine for turbidity testing. The bottom layer (the brine) was then removed and the turbidity determined using a Hach 2100 P Turbidity unit according to API 13J Section 8. (See table 2.)

TABLE 1

Component Listing

| Component | Description |
|---|---|
| Silica flour | silica flour, T&S Materials |
| solids | Rev Dust, Milwhite, Brownsville, Texas |
| IO 16/18 | Isomerized $C_{16}$ to $C_{18}$ alpha-olefins |
| Safe Lube | Brine Lubricant, MI-SWACO, Houston, Texas |
| One Pass A | Solvent/Surfactant Package, MI SWACO, Houston, Texas |
| Brine | Synthetic sea water ASTM D 1141-52 Formula a, Table 1, sec. 4 |

TABLE 2

Testing Results

| Sample | Composition In sea water | Initial Turbidity NTU | Dye-Test Result | Turbidity after Emulsion Breaking NTU |
|---|---|---|---|---|
| Comparative Sample 1 | 0.5 ppb silica flour | 566 | Dot No detectable emulsion | Not run |
| Comparative Sample 2 | 0.5 ppb solids | 660 | Dot No detectable emulsion | Not run |
| Sample 3 | 200 mg/L IO 16/18 100 mg/L Safe-Lube 50 mg/L One Pass A 0.5 ppb silica flour | >1000 | Ring Emulsion detected | 5.75 |
| Sample 4 | 200 mg/L IO 16/18 100 mg/L Safe-Lube 50 mg/L One Pass A 0.5 ppb solids | 888 | Ring Emulsion detected | Not run |
| Sample 5 | 200 mg/L IO 16/18 100 mg/L Safe-Lube 50 mg/L One Pass A 0.05 ppb silica flour | 779 | Ring Emulsion detected | 1.77 |
| Comparative Sample 6 | 0.05 ppb silica flour | 15.8* | Dot No detectable emulsion | Not run |
| Comparative Sample 7 | 0.05 ppb solids | 33.2 | Dot No detectable emulsion | 1.98 |
| Sample 8 | 20 mg/L IO 16/18 10 mg/L Safe-Lube 5 mg/L One Pass A 0.05 ppb silica flour | 20.9 | Ring Emulsion detected | Not run |
| Sample 9 | 20 mg/L IO 16/18 10 mg/L Safe-Lube 5 mg/L One Pass A 0.05 ppb solids | 33.5 | Ring Emulsion detected | 1.78 |
| Sample 10 | 20 mg/L IO 16/18 10 mg/L Safe-Lube 5 mg/L One Pass A | 65.7 | Ring Emulsion detected | 1.30 |
| Comparative Sample 11 | 0.005 ppb silica flour | 2.8* | Dot No detectable emulsion | Not run |
| Comparative Sample 12 | 0.005 ppb solids | 2.79* | Dot No detectable emulsion | Not run |
| Comparative Sample 13 | 2 mg/L IO 16/18 1 mg/L Safe-Lube 0.5 mg/L One Pass A | 3.62* | Dot No detectable emulsion | Not run |

TABLE 2-continued

Testing Results

| Sample | Composition In sea water | Initial Turbidity NTU | Dye-Test Result | Turbidity after Emulsion Breaking NTU |
|---|---|---|---|---|
| Comparative Sample 14 | 0.005 ppb silica flour<br>2 mg/L IO 16/18<br>1 mg/L Safe-Lube<br>0.5 mg/L One Pass A | 5.12* | Dot<br>No detectable emulsion | Not run |
| Comparative Sample 15 | 0.005 ppb solids<br>2 mg/L IO 16/18<br>1 mg/L Safe-Lube<br>0.5 mg/L One Pass A | 4.64* | Dot<br>No detectable emulsion | Not run |

*Initial turbidity less than 20 NTU.

Accordingly, the instant method is capable of detecting the presence of an emulsion in a brine when the turbidity of the brine is about 20 NTU or greater.

It should be understood, of course, that the foregoing relates to preferred embodiments of the invention and that modifications may be made without departing from the spirit and scope of the invention as set forth in the following claims.

What is claimed:

1. A method of detecting an emulsion in a turbid brine, the method comprising the steps of:
    disposing an aliquot of the turbid brine into a sample container to produce a test sample;
    adding one or more drops of a dye solution comprising an oil-soluble dye dissolved in a base oil to said test sample; and
    determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine.

2. The method of claim 1, wherein the turbid brine is a completion fluid.

3. The method of claim 1, wherein the turbid brine comprises a halide salt, a formate salt, or a combination thereof.

4. The method of claim 1, wherein the turbid brine comprises sodium chloride, sodium bromide, sodium formate, potassium chloride, potassium bromide, potassium formate, cesium chloride, cesium bromide, cesium formate, calcium chloride, calcium bromide, zinc chloride, zinc bromide, or a combination thereof.

5. The method of claim 1, wherein the base oil comprises mineral oil, diesel fuel, low-aromatic mineral oil, non-aromatic mineral oil, isomerized $C_{16}$ to $C_{18}$ alpha-olefins, other nonaqueous fluid, or combinations thereof.

6. The method of claim 1, wherein the test sample comprises a 20 ml scintillation vial filled about halfway with the turbid brine.

7. The method of claim 1, wherein the turbid brine is taken from a well in which a lubricant was used in combination with a completion fluid during drilling of the well.

8. The method of claim 1, wherein the turbid brine has a turbidity of greater then or equal to about 20 NTU.

9. The method of claim 1, wherein the oil-soluble dye comprises a lysochrome, a fat-soluble dye, a solvent dye, or a combination thereof.

10. The method of claim 1, wherein the oil-soluble dye comprises Oil Red O, a Sudan dye, Oil Blue A; Oil Blue N, or a combination thereof.

11. A method of detecting an emulsion in a turbid brine, the method comprising the steps of:
    passing an aliquot of the turbid brine through a 0.1 to 10 micron filter to produce a filtered aliquot;
    disposing at least a portion of the filtered aliquot into a clean sample container to produce a test sample;
    adding one or more drops of a dye solution comprising an oil-soluble dye dissolved in a base oil to said test sample; and
    determining the configuration of the dye solution after a period of time on a surface of the test sample, wherein a configuration of the dye solution forming a ring around the perimeter of the sample container at the interface of a wall of the sample container and the turbid brine indicates an emulsion is present in the turbid brine, and wherein a configuration of the dye solution forming a single dot or a plurality of dots on the surface of the turbid brine indicates an emulsion is not present in the turbid brine.

12. The method of claim 11, wherein the 0.1 to 10 micron filter has a maximum porosity of about 1.6 microns.

13. The method of claim 11, wherein the turbid brine is a completion fluid.

14. The method of claim 11, wherein the turbid brine comprises a halide salt, a formate salt, or a combination thereof.

15. The method of claim 11, wherein the turbid brine comprises sodium chloride, sodium bromide, sodium formate, potassium chloride, potassium bromide, potassium formate, cesium chloride, cesium bromide, cesium formate, calcium chloride, calcium bromide, zinc chloride, zinc bromide, or a combination thereof.

16. The method of claim 11, wherein the base oil comprises mineral oil, diesel fuel, low-aromatic mineral oil, non-aromatic mineral oil, isomerized $C_{16}$ to $C_{18}$ alpha-olefins, or combinations thereof.

17. The method of claim 11, wherein the test sample comprises a 20 ml scintillation vial filled about halfway with the turbid brine.

18. The method of claim 11, wherein the turbid brine is taken from a well in which a lubricant was used in combination with a completion fluid during drilling of the well.

19. The method of claim 11, wherein the turbid brine has a turbidity of greater then or equal to about 20 NTU.

20. The method of claim 11, wherein the oil-soluble dye comprises a lysochrome, a fat-soluble dye, a solvent dye, or a combination thereof.

21. The method of claim 11, wherein the oil-soluble dye comprises Oil Red O, a Sudan dye, Oil Blue A; Oil Blue N, or a combination thereof.

22. A method of determining the turbidity of a turbid brine, the method comprising the steps of:
- disposing an aliquot of the turbid brine into a sample container to produce a test sample;
- adding one or more drops of a dye solution comprising an oil-soluble dye dissolved in a base oil to said test sample; and
- determining the configuration of the dye solution after a period of time on a surface of the test sample, wherein a configuration of the dye solution forming a ring around the perimeter of the sample container at the interface of a wall of the container and the turbid brine indicates an emulsion is present in the turbid brine, and wherein a configuration of the dye solution forming a single dot or a plurality of dots on the surface of the turbid brine indicates an emulsion is not present in the turbid brine;
- disposing another aliquot of the turbid brine into a sample container along with an aliquot of an emulsion breaking solvent to produce a centrifuge sample;
- mixing the centrifuge sample by agitation, shaking, or a combination thereof;
- centrifuging the centrifuge sample for a period of time sufficient remove solids which may be present in the turbid brine;
- determining the presence of solids which may have separated from the turbid brine after centrifuging; and
- removing a portion of the brine from the centrifuge sample and determining the turbidity of the brine.

23. The method of claim 22, wherein the emulsion breaking solvent is ethylene glycol mono-butyl ether.

24. The method of claim 22, wherein an aliquot of the turbid brine is first passed through a 0.1 to 10 micron filter prior to being disposed into the sample container to produce the test sample.

25. The method of claim 24, wherein the 0.1 to 10 micron filter has a maximum porosity of about 1.6 microns.

26. The method of claim 22, wherein the turbid brine is a completion fluid.

27. The method of claim 22, wherein the turbid brine comprises a halide salt, a formate salt, or a combination thereof.

28. The method of claim 22, wherein the turbid brine comprises sodium chloride, sodium bromide, sodium formate, potassium chloride, potassium bromide, potassium formate, cesium chloride, cesium bromide, cesium formate, calcium chloride, calcium bromide, zinc chloride, zinc bromide, or a combination thereof.

29. The method of claim 22, wherein the base oil comprises mineral oil, diesel fuel, low-aromatic mineral oil, non-aromatic mineral oil, isomerized $C_{16}$ to $C_{18}$ alpha-olefins, other nonaqueous fluid, or combinations thereof.

30. The method of claim 22, wherein the test sample comprises a 20 ml scintillation vial filled about halfway with the turbid brine.

31. The method of claim 22, wherein the turbid brine is taken from an oil well in which a lubricant was used in combination with a completion fluid during drilling of the oil well.

32. The method of claim 22, wherein the turbid brine has a turbidity of greater then or equal to about 20 NTU.

33. The method of claim 22, wherein the oil-soluble dye comprises a lysochrome, a fat-soluble dye, a solvent dye, or a combination thereof.

34. The method of claim 22, wherein the oil-soluble dye comprises Oil Red O, a Sudan dye, Oil Blue A; Oil Blue N, or a combination thereof.

* * * * *